United States Patent [19]

Enhorning

[11] Patent Number: 5,685,843

[45] Date of Patent: Nov. 11, 1997

[54] APPARATUS FOR PERFORMING BRONCHO-ALVEOLAR LAVAGE AND METHOD OF USING

[75] Inventor: Goran E. Enhorning, Buffalo, N.Y.

[73] Assignee: The Research Foundation of State University of New York, Amherst, N.Y.

[21] Appl. No.: 423,461

[22] Filed: Apr. 19, 1995

[51] Int. Cl.$^6$ .......................... A61M 31/00; A61M 1/00
[52] U.S. Cl. .......................... 604/54; 604/121; 604/181
[58] Field of Search ................................ 604/19, 23, 27, 604/28, 30, 35, 36, 38, 48, 49, 50, 54, 171, 181, 187, 264, 270, 280–284, 183–184, 118–119, 121; 128/897, 898

[56] References Cited

U.S. PATENT DOCUMENTS

| | | | |
|---|---|---|---|
| 1,231,772 | 7/1917 | Meyer | 604/38 |
| 4,525,156 | 6/1985 | Benusa et al. | 604/28 |
| 4,701,160 | 10/1987 | Lindsay et al. | 604/53 |
| 4,734,091 | 3/1988 | Boyle et al. | 604/54 |
| 4,821,714 | 4/1989 | Smelser | 128/207.14 |
| 4,953,547 | 9/1990 | Poole, Jr. | 128/203.12 |
| 5,002,528 | 3/1991 | Palestrant | 604/28 |
| 5,037,399 | 8/1991 | Reichert et al. | |
| 5,135,490 | 8/1992 | Strickland | |
| 5,165,420 | 11/1992 | Strickland | |
| 5,246,012 | 9/1993 | Strickland | |
| 5,356,375 | 10/1994 | Higley | 604/30 |

*Primary Examiner*—Mark Bockelman
*Attorney, Agent, or Firm*—John C. Thompson

[57] ABSTRACT

Apparatus for performing broncho-alveolar lavage and method of using the apparatus using relatively low known pressures which may avoid damage, such as overexpansion and rupture of airways and alveoli, when too high a pressure is used. The apparatus includes a closed barrel device for receiving a predetermined quantity of broncho-alveolar lavage fluid, apparatus for applying a predetermined pneumatic pressure upon the upper surface of the broncho-alveolar lavage fluid, and a catheter, the distal end of which may be properly positioned in the portion of a patient's lung to be lavaged. The pressure applying apparatus includes a closed compartment forming an air chamber, and a fluid containing first bladder mounted within the air chamber, the air chamber being in communication with the closed air space in the barrel device above the lavage fluid. The hydraulic pressure applying device is a second bladder in an open container in fluid connection with the first bladder. In use, it is now only necessary to raise the open container a certain height above the closed container to cause fluid to flow from the second bladder to the first bladder pressurizing the air chamber. As this chamber is connected with the chamber in the syringe, the broncho-alveolar lavage fluid will be pressurized to this extent and be forced through the catheter into the lung. When the lavage fluid is aspirated into the syringe, the open container is lowered below the level of the closed container.

3 Claims, 2 Drawing Sheets

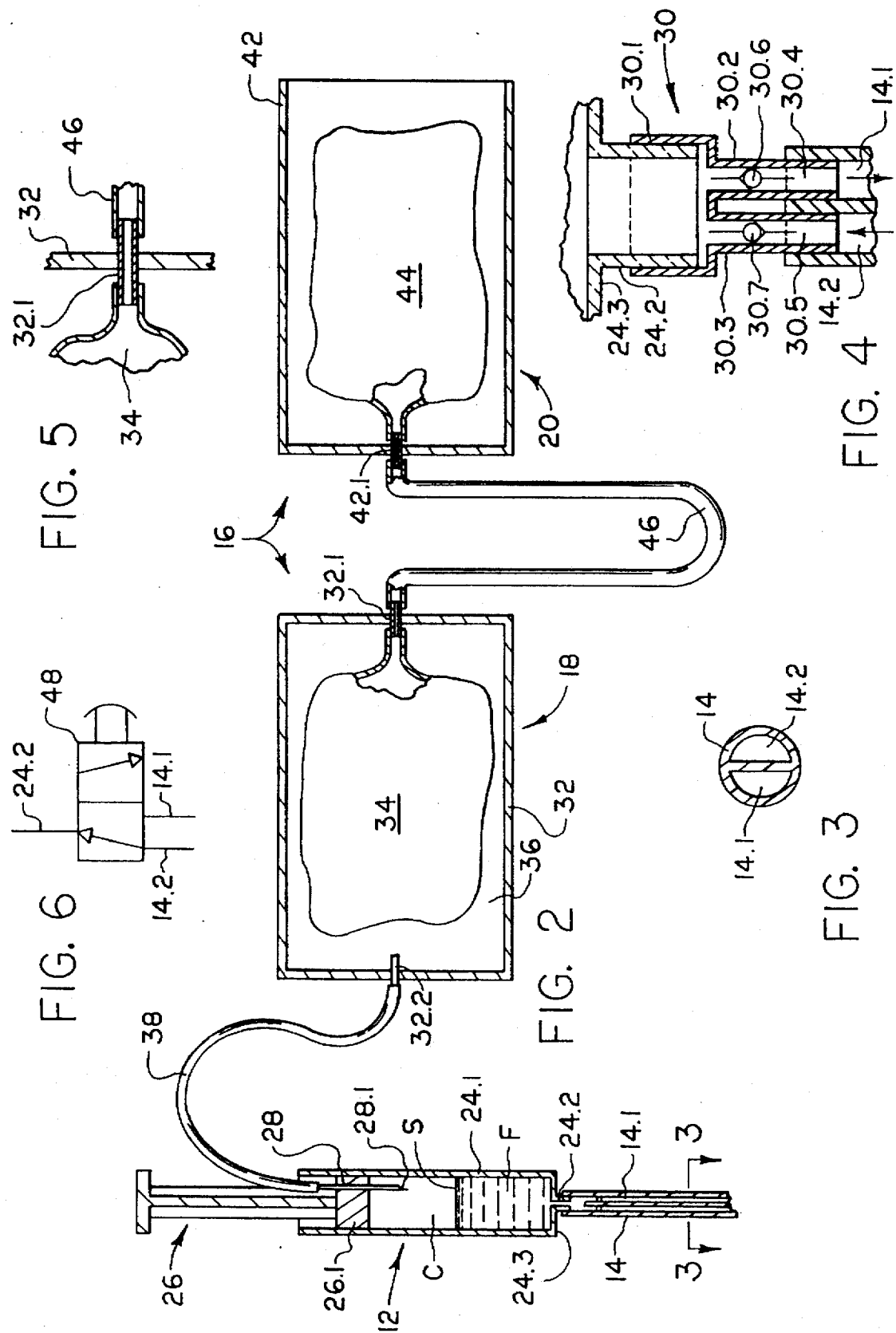

APPARATUS FOR PERFORMING BRONCHO-ALVEOLAR LAVAGE AND METHOD OF USING

TECHNICAL FIELD

This invention relates generally to an apparatus for performing broncho-alveolar lavage and method of using the apparatus, and more particularly to a method and apparatus for performing such a lavage using relatively low known pressures which may avoid damage, such as overexpansion and rupture of airways and alveoli, when too high a pressure is used.

BACKGROUND OF THE INVENTION

Broncho-alveolar lavage is an examination which is being used increasingly to analyze cells and biochemical agents present in peripheral airways. An apparatus for performing such lavage is shown in U.S. Pat. Nos. 5,135,490, 5,165,420 and 5,246,012. The patented apparatus includes a broncho-alveolar lavage catheter, the distal end of which can be properly positioned in the lung of a patient. After it has been properly positioned, fluid from a reservoir is infused with a syringe and is then aspirated, either with the syringe or with vacuum from a wall outlet in the medical institution where the lavage is conducted. When using a syringe for infusion, it is a considerable risk that too much pressure will be applied causing overexpansion and rupture of airways and alveoli. If there is such a rupture, a portion of the infused lavage fluid will be lost from the airway catheter and the fluid remaining in the airways is likely to become contaminated by body fluids.

OBJECTS AND SUMMARY OF THE INVENTION

It is an object of the present invention to provide an apparatus which makes it possible to carry out broncho-alveolar lavage with known pressures which are controlled to be within a range that will not damage or rupture airways or alveoli.

More specifically, according to one aspect of the present invention, it is an object of the present invention to provide an assembly for performing broncho-alveolar lavage or the like, which assembly uses relatively low, predetermined pressures, preferably in the range of approximately ±30 cm of water pressure. The broncho-alveolar lavage assembly includes a closed barrel device for receiving a predetermined quantity of broncho-alveolar lavage fluid. At the bottom of the barrel device is a port. Above the broncho-alveolar lavage fluid is a closed air space where pressure can be altered. Pressure applying means are provided which are capable of applying a predetermined pneumatic pressure upon the upper surface of the broncho-alveolar lavage fluid within the range from approximately 30 cm of positive water pressure to approximately 30 cm of negative pressure, which pressures will not cause damage to the airways or the alveoli, and which pressures can be regulated with great accuracy. (While 30 cm of negative pressure is within the range of the apparatus disclosed, as a practical matter, 20 cm of negative pressure has been found to be well within acceptable limitations.) The broncho-alveolar lavage assembly further includes a catheter, one end of which is connected to the port of the barrel device, the distal end of which can be properly positioned in the portion of a patient's lung to be lavaged. When the pressures are raised broncho-alveolar lavage fluid will enter and expand the airways of the lung. When pressure is lowered the broncho-alveolar lavage fluid will be sucked back into the barrel.

It is a further object of the present invention to provide an apparatus of the type set forth above wherein the pressure applying means includes hydraulic pressure applying means and pressure converting means for converting hydraulic pressure to pneumatic pressure. The pressure converting means includes a fluid containing first thin walled flaccid bladder mounted in a closed compartment having an air chamber therein. The hydraulic pressure applying means is connected to the first thin walled bladder for applying either a positive or negative hydraulic pressure to the pressure converting means, the hydraulic pressure applying means being a second bladder in an open container. The air chamber in the closed compartment may be the closed air space in the closed barrel device, or it may be separate from the closed air space, in which case it is connected by suitable pneumatic passageways.

More specifically, the pressure of the air in the closed container, and thus in the barrel, can be altered by changing the amount of liquid expanding the bladder. Such a change is achieved by altering the level of a second liquid filled bladder. This second bladder is protected by being housed in a second open container. By elevating this second container in relation to the first, water will run into the bladder of the air chamber, thereby raising pressure in the air in the barrel. With the same mechanism air pressure in the barrel can be diminished by lowering the open container.

It is a further object of the present invention to provide a method of performing broncho-alveolar lavage by providing the apparatus set forth above in the three preceding paragraphs, by inserting the distal end of the catheter into the portion of the lungs to be lavaged; by raising the open container which carries the second bladder a limited amount to a position above the pressure converting means to cause a positive pneumatic pressure to be applied to the surface of the broncho-alveolar lavage fluid, whereby the lavage fluid will be caused to flow from the closed barrel device through the catheter into the lungs; by lowering the open container a limited amount relative to the pressure converting means to a position below the pressure converting means to cause a negative pneumatic pressure to be applied to the surface of the broncho-alveolar lavage fluid, causing lavage fluid to be suctioned from the lungs through the catheter and back into the closed barrel device; and repeating the steps set forth above until a desired concentration of broncho-alveolar lavage fluid is collected in the closed barrel device. With the arrangement described, the operator of the broncho-alveolar lavage assembly can closely control both infusion and aspiration pressure by moving the second bladder in the open compartment relative to the first bladder in the closed compartment. Thus, the operator of the broncho-alveolar lavage can, after introducing the catheter into a particular airway branch, allow the lavage fluid to expand the section of the lung supplied by the chosen airway branch, with a closely controlled pressure. The lavage fluid can then be returned with a closely controlled suction.

The foregoing objects and other objects and advantages of this invention will be more fully understood from a consideration of the following figures which illustrate a preferred embodiment of this invention.

BRIEF DESCRIPTION OF THE DRAWINGS

FIG. 2 is an enlarged view, partially in section, showing the apparatus of the present invention.

FIG. 3 is a section along the line 3—3 in FIG. 2, showing a double lumen catheter.

FIG. 4 is an enlarged section of a portion of FIG. 2, this view showing a first valve assembly used with a double lumen catheter.

FIG. 5 is an enlarged section of a portion of FIG. 2.

FIG. 6 is a schematic view of an alternate valve assembly which may be used with the double lumen catheter.

DETAILED DESCRIPTION

Figure 1:
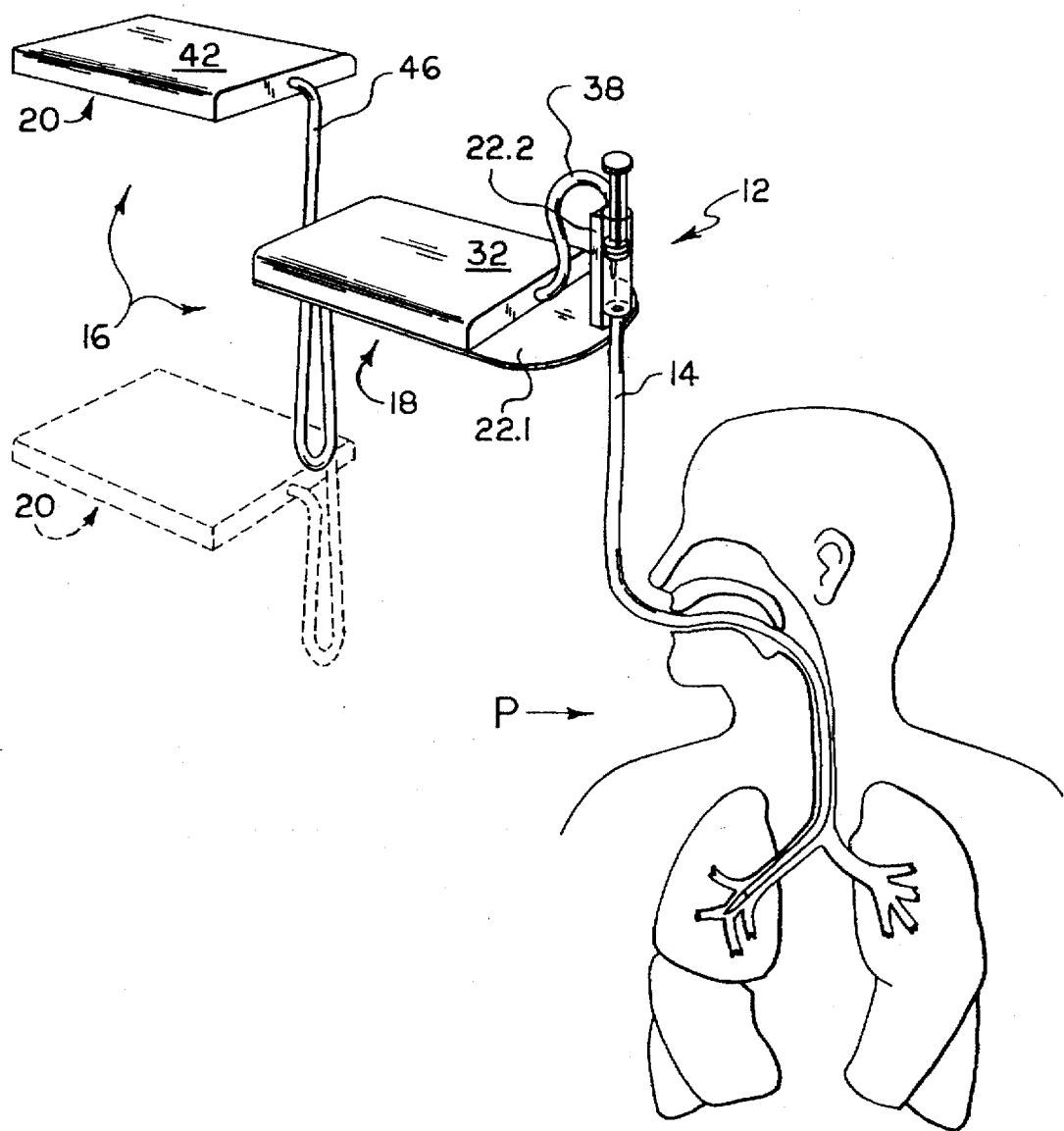
FIG. 1 is a schematic drawing illustrating how a broncho-alveolar lavage may be conducted using the apparatus and method of the present invention.

FIG. 1 is an overview of the system for performing broncho-alveolar lavage, the system being indicated generally at 10. Three principal assemblies are noted: a closed barrel device, indicated generally at 12, a catheter 14, and a pressure applying means, indicated generally at 16. The pressure applying means in turn includes two sub-assemblies, namely pressure-converting means indicated generally at 18 and hydraulic pressure applying means indicated generally at 20. In addition to the foregoing operative components, the apparatus of this invention in the preferred embodiment also includes a support having a horizontal portion 22.1 and a vertical portion 22.2.

In the preferred design illustrated, the closed barrel device is a syringe. The barrel of the syringe is secured to the vertical portion 22.2 of the support in any conventional manner. The syringe includes a syringe plunger 26 having a piston 26.1 slidable within the cylindrical portion 24.1 of the barrel. The barrel is also provided with a fluid port 24.2 in the form of a cylindrical extension to the bottom 24.3 of the syringe. The closed barrel device 12 further includes pneumatic passageway means in the form of a hollow needle 28, the lower end 28.1 of the needle being disposed below the piston 26.1 within a closed air space C disposed above the upper surface S of the broncho-alveolar lavage fluid F within the barrel. In practice, a conventional syringe needle is passed through the piston. After it has been passed through the piston, the lower end is cut off and the remaining needle below the piston is flared to prevent it from being withdrawn.

A single lumen catheter may be used, but a double lumened catheter as shown in FIG. 3 is preferred. Thus, one lumen 14.1 may be used for infusion and the other 14.2 for aspiration. The hilt or proximal end of the catheter is connected to the port 24.2 via an adapter indicated generally at 30. The adapter has an upper cylindrical section 30.1 which may be slipped about the fluid port 24.2 in a fluid tight manner. Below the upper section 30.1 are two D-shaped portions 30.2, 30.3 which may be received within the infusion and aspiration lumens 14.1 and 14.2, respectively. Each of the D-shaped portions 30.2 and 30.3 are in turn provided with passageways 30.4, 30.5, respectively. Each of the passageways 30.4, 30.5 is provided with a check valve 30.6, 30.7, respectively. The check valve 30.6 will permit only infusing flow, and the valve 30.7 will permit only aspiration flow. The check valves are only illustrated schematically and the actual details of the check valves 30.6 and 30.7 form no part of the present invention.

As previously indicated, the pressure applying means 16 consists of two sub-assemblies. The pressure converting means, which are indicated generally at 18, include a closed air-tight compartment 32. Disposed within the air-tight compartment is a soft walled first bladder 34, partly filled with a hydraulic fluid, such as water. One end of the bladder 34 is connected with a hydraulic port 32.1, in the form of a tube which extends through a sidewall of the compartment 32. As can be seen from FIG. 2, the first bladder 34 does not entirely fill the air-tight container 32 and there is an air chamber 36 extending between the bladder 34 and a pneumatic port 32.2. The closed compartment 32 is preferably mounted upon the horizontal upper surface of the horizontal support portion 22.1. A first tube 38 extends between a pneumatic port 32.2 and the pneumatic pressure means or needle 28, the pneumatic port 32.2 being similar to the hydraulic port 32.1.

The hydraulic pressure applying means consists of a compartment 42 open to atmosphere, the compartment also being provided with a hydraulic port 42.1 similar to the port 32.1. A second bladder 44 is loosely contained within the second compartment. The second bladder is in turn connected with the hydraulic port 42.1. The ports 32.1 and 42.1 are in turn connected to each other via a long flexible tube 46.

The apparatus of the present invention may be used in the manner which will be described below. This invention will be described with a human patient, indicated generally at P. However, the apparatus may also be used for research with animals, etc. The catheter will be passed through the patient's trachea until the distal end is properly wedged into a branch of the bronchial tree. Prior to insertion of the catheter 14 into the lungs, the syringe 12 is filled with the desired quantity of broncho-alveolar lavage fluid which is to be used. This is done by lowering compartment 42 to under the level of compartment 32 which will cause the desired amount of broncho-alveolar lavage fluid to be aspirated into the barrel of the syringe. Once the desired amount has been aspirated tube 38 is clamped with a hemostat. To infuse the desired portion of the lungs with broncho-alveolar lavage fluid, it is now only necessary after removing the hemostat on tube 38, to raise the open container 42 to a certain height, for example 25 cm above the closed container 32. Fluid will flow from the second bladder 44 to the first bladder 34 pressurizing the air chamber 36 to 25 cm water pressure. As this chamber is connected with the chamber C in the syringe, the broncho-alveolar lavage fluid will also be pressurized to this extent and will be forced through the catheter into the lung. When the lavage fluid is to be sucked back into the syringe, compartment 42 is lowered below the level of compartment 32. The broncho-alveolar lavage fluid will now be aspirated from the lungs. This process can be repeated a number of times to give the broncho-alveolar lavage fluid a high concentration of cells and chemical agents. By utilizing the double-lumened catheter the effect of a large dead space can be avoided.

Instead of using the adapter 30 with the check valves 30.6 and 30.7, it would be possible to use a three way stopcock illustrated schematically at 48 in FIG. 6, which will be in a first position when pressure is raised, and in a second position when pressure is lowered. Thus, when the stopcock is in the first position (not shown) lavage fluid will pass through lumen 14.1 to the lung, and when the stopcock is in the second position (shown schematically in FIG. 6) liquid will return to the barrel.

While an apparatus used in a laboratory has been disclosed in this application, it should be noted that other forms of apparatus may be employed. For example, the closed barrel device may be formed of components other than a syringe. In addition, in an alternative design the closed barrel device may receive a first soft walled bladder, preferably in the shape of a bellows, equivalent in function to the soft walled first bladder 34, the first soft walled bladder being in turn connected to a second soft walled bladder containing a liquid, the second soft walled bladder being equivalent in function to the bladder 44. When the second bladder of the alternative design is 35 raised relative to the first soft walled bladder, fluid will flow into the first soft walled bladder causing the air within the closed barrel device to be pressurized. This will in turn pressurize the broncho-alveolar lavage fluid within the closed barrel device, the alternative design functioning in the same manner as the laboratory apparatus described above. Other variations will occur to those having ordinary skill in the art. Therefore, it should be understood that the applicant does not intend to be limited to the particular details described above and illustrated in the accompanying drawings, but intends to be limited only to the scope of the invention as defined by the following claims.

What is claimed is:

1. A method of performing broncho-alveolar lavage comprising the following steps:
    a) providing a broncho-alveolar lavage assembly including
        a closed barrel device containing a predetermined quantity of broncho-alveolar lavage fluid, the barrel device being provided with a port below the surface of the broncho-alveolar lavage fluid, a closed air space above the broncho-alveolar lavage fluid, and fluid passageway means in communication with the closed air space,
        a catheter connected to the port,
        pressure converting means for converting hydraulic pressure to pneumatic pressure, the pressure converting means including a hydraulic port,
        hydraulic pressure applying means in the form of a hydraulic fluid container having a port, and
        a second tube extending between the port of the hydraulic fluid container and the hydraulic port of the pressure converting means;
    b) connecting the catheter with the portion of the lungs to be lavaged;
    c) raising the hydraulic fluid container a limited amount to a position above the pressure converting means to raise the pressure in the closed air space above the broncho-alveolar lavage fluid to cause the lavage fluid to flow from the closed barrel device through the catheter into the lungs;
    d) lowering the hydraulic fluid container a limited amount relative to the pressure converting means to a position below the pressure converting means to lower the pressure in the closed air space above the broncho-alveolar lavage fluid to cause lavage fluid to be suctioned from the lungs through the catheter and back into the closed barrel device; and
    e) repeating steps c and d until a desired concentration of broncho-alveolar lavage fluid is collected in the closed barrel device.

2. An assembly which may be used for performing broncho-alveolar lavage, which assembly uses pressures in the range of ±30 cm of water pressure; said assembly comprising:
    a cylindrical syringe barrel for receiving a predetermined quantity of broncho-alveolar lavage fluid, the barrel being provided with a port which would be below the surface of the broncho-alveolar lavage fluid when fluid is within the barrel;
    a syringe plunger having a piston slidable within the barrel, there being a closed air space above the piston where pressure can be varied, and fluid passageway means passing through the piston in communication with the closed air space;
    a catheter, one end of which is connected to the port, and the other end of which may be operatively connected to the lungs which are to be lavaged; and
    pressure applying means capable of altering the pressure in the closed air space above the piston an entire pressure range from a positive pressure of approximately 30 cm of water pressure to a negative pressure of approximately 30 cm of water pressure, a portion of the pressure applying means being connected to the fluid passageway means.

3. The assembly for performing broncho-alveolar lavage or the like as set forth in claim 2 wherein the pneumatic passageway means is a hollow needle.

* * * * *